United States Patent [19]
Ghezzi et al.

[11] Patent Number: 5,194,157
[45] Date of Patent: Mar. 16, 1993

[54] BLOOD PURIFYING EQUIPMENT PARTICULARLY FOR THE TREATMENT OF PATIENTS SUFFERING FROM RENAL INSUFFICIENCY, AND A METHOD OF PRODUCING A REINFUSION LIQUID FOR HAEMODIAFILTRATION (HDF)

[75] Inventors: Paolo Ghezzi, Peveragno; Renzo Gervasio, Turino, both of Italy

[73] Assignee: Sorin Biomedica Emodialisi SRL, Luggia, Italy

[21] Appl. No.: 884,879

[22] Filed: May 18, 1992

Related U.S. Application Data

[63] Continuation of Ser. No. 640,262, Jan. 11, 1991, abandoned.

[30] Foreign Application Priority Data

Mar. 9, 1990 [IT] Italy .................................. 67168 A/90

[51] Int. Cl.⁵ ............................................. B01D 61/00
[52] U.S. Cl. ................................... 210/646; 210/198.1;
210/257.2; 210/259; 210/314; 210/321.64;
210/321.65; 210/321.72; 210/641; 210/650;
210/652; 210/929; 422/44
[58] Field of Search ............... 210/641, 646, 647, 650,
210/652, 198.1, 257.2, 259, 314, 321.64, 321.65,
321.72-321.9, 929; 604/4, 5, 6; 422/44

[56] References Cited

U.S. PATENT DOCUMENTS

| | | | |
|---|---|---|---|
| 3,579,441 | 5/1971 | Brown | 210/929 |
| 3,799,873 | 3/1974 | Brown | 210/641 |
| 4,218,321 | 8/1980 | Sasaki et al. | 210/321.72 |
| 4,397,747 | 8/1983 | Ikeda | 210/641 |
| 4,702,841 | 10/1987 | Sengbusch | 210/434 |
| 4,708,714 | 11/1987 | Larsson et al. | 604/5 |
| 4,728,430 | 3/1988 | DiLeo et al. | 210/641 |
| 4,839,055 | 6/1989 | Ishizaki et al. | 210/641 |
| 4,923,598 | 5/1990 | Schäz | 210/321.65 |

FOREIGN PATENT DOCUMENTS

| | | |
|---|---|---|
| 222709 | 5/1987 | European Pat. Off. . |
| 206076 | 1/1984 | Fed. Rep. of Germany . |
| 2585251 | 1/1987 | France . |

*Primary Examiner*—Robert A. Dawson
*Assistant Examiner*—Sun Uk Kim
*Attorney, Agent, or Firm*—George P. Hoare, Jr.

[57] ABSTRACT

Blood to be purified is passed through a haemofiltration element and a haemodialysis element in cascade and the ultrafiltrate output from the haemofiltration element is passed through a filter such as an activated carbon filter, preferably with uncoated activated carbon. The ultrafiltrate thus purified can then be used as a reinfusion solution to be readministered to the patient.

27 Claims, 5 Drawing Sheets

BLOOD PURIFYING EQUIPMENT PARTICULARLY FOR THE TREATMENT OF PATIENTS SUFFERING FROM RENAL INSUFFICIENCY, AND A METHOD OF PRODUCING A REINFUSION LIQUID FOR HAEMODIAFILTRATION (HDF)

This is a continuation of application Ser. No. 07/640,262, filed on Jan. 11, 1991, now abandoned.

The present invention relates in general to the purification of blood, for example, in patients suffering from renal insufficiency.

In this connection, the solution according to the present invention constitutes a development of the solution described in Italian utility model No. 198528.

In this prior-art solution, which has had considerable clinical success, the blood to be purified is passed through a haemofiltration element and a haemodialysis element which are interconnected in series (in cascade) with respect to the blood flow.

In both elements, the blood to be purified is brought into contact with membranes which have certain degrees of permeability as regards the toxic substances to be eliminated. The toxic substances can pass through the membrane by two distinct physical processes, that is to say, by diffusion or by convection.

In the haemodialysis element, the dominant process is diffusion. In fact, haemodialysis is carried out with membranes constituted, for example, by the material known by the trade name of "Cuprophan" or the like and with a circuit in which the blood to be purified passes along one side of the membranes and a washing solution passes along the other side. The membranes used have high diffusion coefficients for small molecules, such as those of urea, and low diffusion coefficients for medium-large molecules (molecular weights greater than 1000). Their ultrafiltration coefficients are low. The purification achieved by haemodialysis in the patient under treatment is good as regards urea but poor as regards toxic substances with medium-high molecular weights and there is a limited loss of body weight.

The dominant process in the haemofiltration element is convection. In fact, haemofiltration is effected with very porous synthetic membranes and with a blood-flow circuit which creates a pressure gradient through the membrane (currently known as the TMP) and eliminates the ultrafiltrate without the need to use a washing solution. Large quantities of liquid are therefore eliminated (about 20-30 liters during a complete treatment) and both the small and the medium-large molecules are entrained therewith. In order to compensate for the excessive loss of water, it is therefore necessary continuously to infuse solutions of a suitable composition into the patient's blood so as to achieve the desired final loss of body weight.

Combined purifying techniques also exist, such as that known as haemodiafiltration which is comparable to a combination of the haemodialysis and haemofiltration techniques described above and is carried out with membranes similar to those used in haemofiltration. Structurally, this technique is comparable to haemodialysis but, as a result of the greater permeability of the membrane used, the ultrafiltration is more significant (although less than that which occurs in haemofiltration) and it is thus also necessary to infuse a solution of suitable composition into the blood to compensate for the loss.

The solution of the aforesaid utility model 198528 is based on a combined haemodialysis-haemofiltration technique and has some considerable advantages, such as the fact that the two filter elements can be controlled separately. In fact, the haemodialysis element is connected to normal haemodialysis equipment with a low or zero TMP. The haemofiltration element, however, is associated with a blood-flow circuit which establishes the TMP on the basis of the quantity of ultrafiltrate desired.

The solution of suitable composition which compensates for the eccessive loss of body weight in the patient can be infused at a point in the blood-flow circuit intermediate the two filters. Thus, a precise equilibrium of the concentrations of salts in the purified blood and in the washing solution can easily be established in the haemodialysis element which is usually situated downstream. In fact ions (sodium, potassium, etc . . . ) are exchanged easily between the blood and the washing solution through the membranes of the haemodialysis element. In haemofiltration and haemodiafiltration equipment, however, it is much more difficult to achieve a precise control of the salt concentrations in the blood which is returned to the body after purification.

Finally, the overall efficiency of the combined haemodialysis-haemofiltration equipment is very high.

The need to infuse a solution of suitable composition to compensate for the loss of body weight caused by the convection which dominates in haemofiltration, however, creates objective difficulties of an operational nature.

As well as obvious problems of cost and storage as far as the structures for treating kidney disease are concerned, the infusion of the solution is not without a risk of pyrogenic effects and the like. Moreover, in any case, there is a certain difficulty in the precise regulation of the electrolytic characteristics of the compensation solution in order to prevent disequilibrium when it is reinfused into the patient's body.

The object of the present invention is to provide means which solve the aforementioned problems in an ideal manner without foregoing the advantages of the combined haemodialysis-haemofiltration technique described above.

According to the present invention, this object is achieved by virtue of equipment and a method having the characteristics claimed specifically in the claims which follow.

The invention will now be described with reference to the appended drawings, in which.

Figure 1:
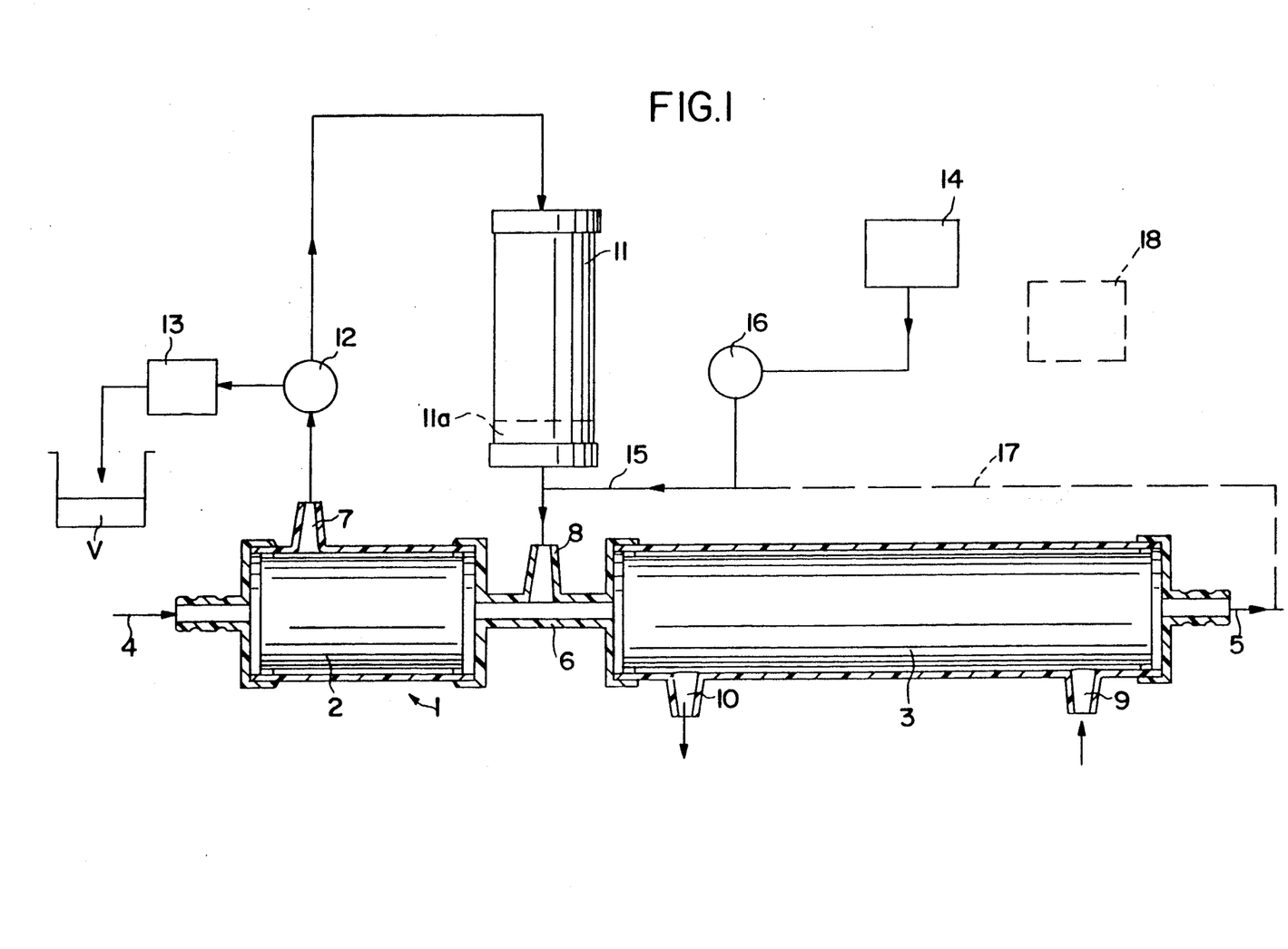
FIG. 1 shows the structure of equipment according to the invention in diagrammatic form.

In the drawing, equipment for purifying blood by a combined haemodialysis-haemofiltration technique is generally indicated 1.

Essentially, the equipment 1 comprises a haemofiltration element 2 and a haemodialysis element 3 which are arranged in series (in cascade) with respect to the flow of liquid between an inlet connector 4 and an outlet connector 5 for connecting the equipment in a flow-line which draws blood to be purified from the patient's body and subsequently returns the purified blood to the patient's body.

For a more detailed description of these elements reference may usefully be made to the Italian utility model No. 198528 cited above and to the technical solutions claimed therein.

This also applies to the arrangement of a tubular duct 6 which interconnects the elements 2 and 3, actually integrating them in a single device.

In brief, the blood to be purified, which is introduced into the haemofiltration element 2 through the inlet connector 4, passes into the duct 6 after haemofiltration and thence into the haemodialysis element 3 which is situated downstream with respect to the flow of liquid and outputs the purified blood through the outlet connector 5.

The ultrafiltration products (the ultrafiltrate) resulting from the action of the element 2 are output therefrom through an outlet connector 7.

A connector 8, however, enables a reinfusion solution of suitable composition to be introduced into the duct 6 so that it can pass into the haemodialysis element 3 in order partially or wholly to compensate for the losses caused by the ultrafiltration. According to the present invention, this solution is produced by the regeneration of the ultrafiltrate by criteria which will be described further below.

According to a widely-known solution, however, inlet and outlet connectors, indicated 9 and 10 respectively, are provided for the passage of the washing solution for carrying out the haemodialysis process in the element 3.

Essentially, the present invention is based on the realisation that the ultrafiltrate withdrawn from the outlet duct 7 of the element 2 can be regenerated by its being passed through a filter (a regenerator element) 11 so that it can be used as an infusion solution. In the prior art, on the other hand, this solution, which is prepared pharmaceutically, is taken in from outside.

More precisely, the ultrafiltrate output through the connector 7 is supplied to the filter 11 through a pump 12. The pump has a discharge connector 13 for discharging some of the ultrafiltrate to the outside should this be necessary for various reasons (for example, at the start of the purification cycle, etc . . . ). The ultrafiltrate drawn off through the connector 13 is collected in a discharge container V.

A container, indicated 14, is intended to contain electrolytic solutions and/or buffer solutions which may be pumped by a pump 16 through a duct 15 opening into the line leading to the connector 8 so as to be added to the regenerated ultrafiltrate output from the filter 11.

Instead of being sent to the line 15 which ends upstream of the haemodialysis element 3 with respect to the flow of liquid, the solution in the container 14 may be sent through a line 17 which opens downstream of the element 3 before the purified blood is returned to the patient's body.

This also applies to the arrangement of any so-called "buffer free" system 18 for the administration of electrolytes and buffer solutions downstream of the entire haemofiltration-haemodialysis unit. In this case, this takes place through the line 17.

In the solution according to the invention, the ultrafiltrate which is produced by the pressure gradient during the passage of the blood through the element 2 and contains solutes with medium-high molecular weights (including beta-2-microglobulin) is regenerated by its passage through the filter 11. In the embodiment preferred at present, this is constituted essentially by a cartridge of coated or—even better—uncoated activated carbon which can retain the solutes contained in the ultrafiltrate by adsorption.

The filter 11 may, to advantage, be constituted by an (uncoated) carbon haemoperfusion cartridge which has been sold for several years under the trade name of Detoxyl 2 by Sorin Biomedica S.p.a. of Saluggia (Vercelli), Italy.

The ultrafiltrate thus purified can then be used as a reinfusion solution and readministered to the patient.

The very heavy solute molecules thus undergo the following process:
removal from the blood by haemofiltration,
purification by adsorption on carbon,
administration to the patient in purified form.

An "endogenous" replacement liquid containing electrolytes and bicarbonates can be produced and, with obvious advantages, can replace the "exogenous" physiological electrolyte solution (normally prepared pharmaceutically) used in the prior art.

The adsorption is effected on ultrafiltrate which has no red corpuscles, white corpuscles, platelets, fibrinogen, proteins, etc. Thus, the biocompatibility problems which activated carbon has shown towards blood in the past do not arise in the solution according to the invention. These problems have lead some people to propose the use of filter cartridges which have activated carbon coated with various materials (collodion, etc.) but with final results which cannot be considered satisfactory.

Activated (uncoated) carbon shows an excellent ability to adsorb the solutes contained in the ultrafiltrate, particularly as regards beta-2-microglobulin and myoglobin (molecular weights of about 20,000 daltons).

In any case, the risk of active carbon granules being administered to the patient as a result of the reintroduction of the purified ultrafiltrate can be eliminated by a filter element of suitable porosity which may be constituted, for example, by a simple gauze associated with the output of the filter 11. Such a filter is normally provided in the Detoxyl product mentioned above.

In general, the activated carbon of the filter 11 is produced from various natural substances (lignite, anthracite, peat, petroleum, etc.) which have undergone oxidation treatments which give them good adsorption capabilities. The final product is in the form of microgranules, each of which has a multitude of minute channels opening in corresponding pores on its surface. The contact surface developed by virtue of this structure is very large, up to 1000 $m^2$ per gram of carbon. The molecules are adsorbed by physico-chemical mechanisms consisting essentially of the trapping of the molecules in the channels. The adsorption spectrum of activated carbon extends to substances with molecular weights of between 100 and 20,000 daltons. The maximum adsorption is of molecules with weights of between 300 and 1500 daltons, identified clinically as "medium molecules", which are present in abnormal quantities in uraemic patients and are incompletely removed by the dialysis membrane (element 3) by diffusion mechanisms.

As already stated, activated carbon in the form described must be considered to have poor biocompatibility and thus to have very poor haemocompatibility. In fact, in contact with the blood, it causes depletion of the erythrocytes, platelets, white corpuscles, fibrinogen and other substances of biological value. Moreover, in circulation, it releases microembolisms which cause rigor, fevers and the accumulation of carbon in the reticuloendothelial systems of the patients.

For these reasons, activated carbon was used sporadically for haemoperfusion until the 60s when Chang proposed and carried out a method of coating the individual granules with a polymer based on albumin and cellulose (collodion). The coatings most generally used are albumin, cellulose and methacrylate. Although, on the one hand, these coating systems provide the activated carbon with good biocompatibility, on the other hand, they restrict its adsorption capabilities since the coating film restricts the passage of solutes with high molecular weights and above all of beta-2-microglobulin whose accumulation in the body a uraemic patient, has great importance in determining the typical pathology of a haemodialysed subject (amyloidosis).

From this point of view, therefore, the present invention goes against the general opinion in the art by proposing the preferential use of uncoated activated carbon to form the filter 11. This is because the filter is not brought into direct contact with the blood but, on the contrary, is only in contact with the haemofiltrate output from the element 2.

Figure 2A:
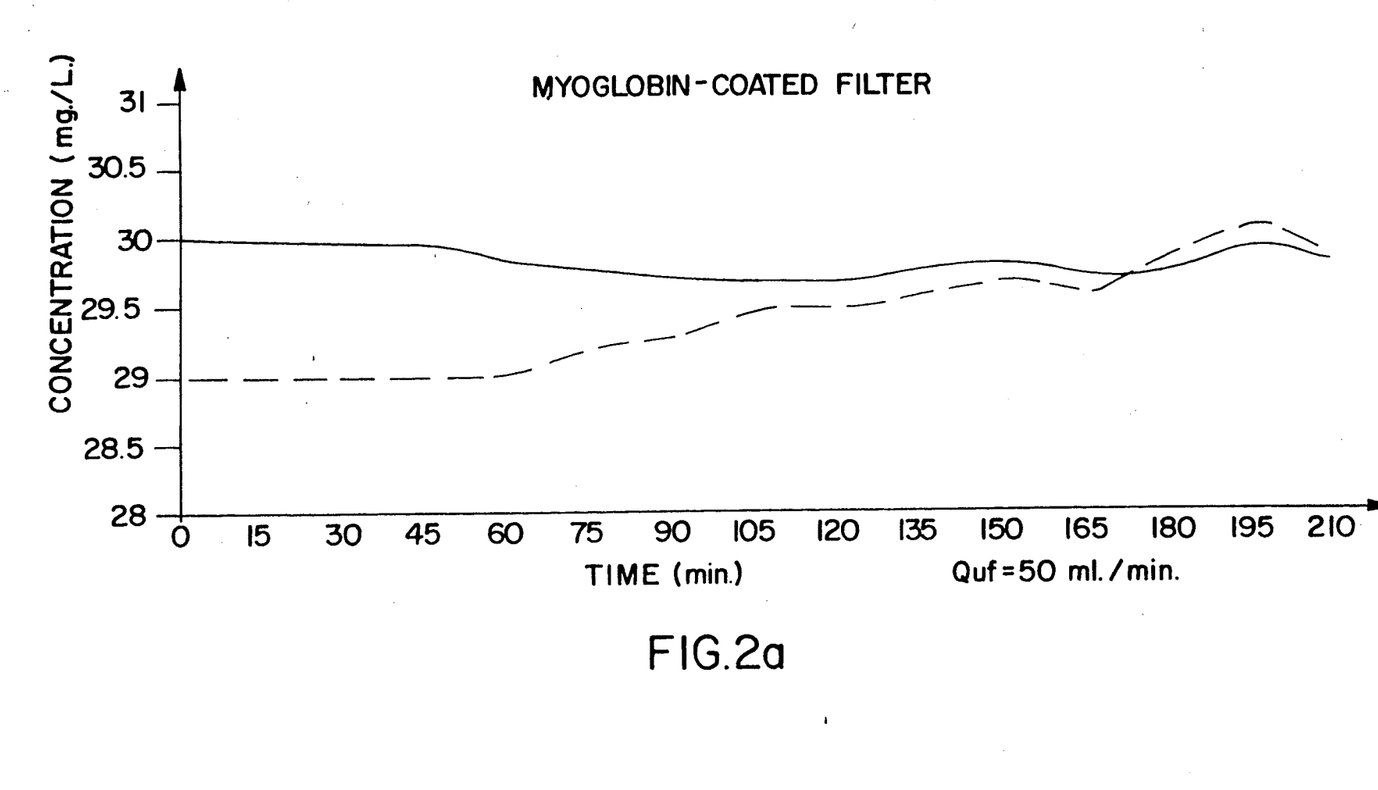
FIGS. 2a, 2b, 3a and 3b are graphs showing the efficiency of the purification which can be achieved according to the invention.
Figure 2B:
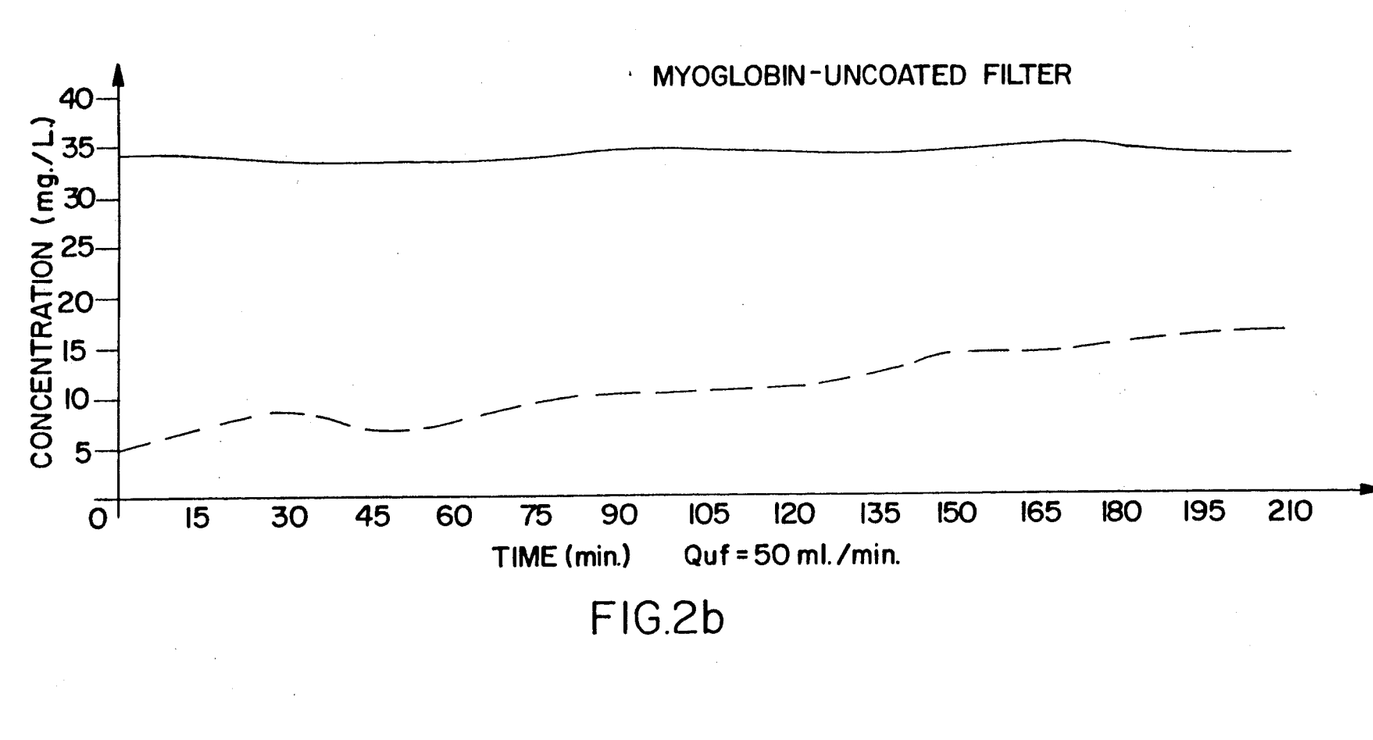
Figure 3A:
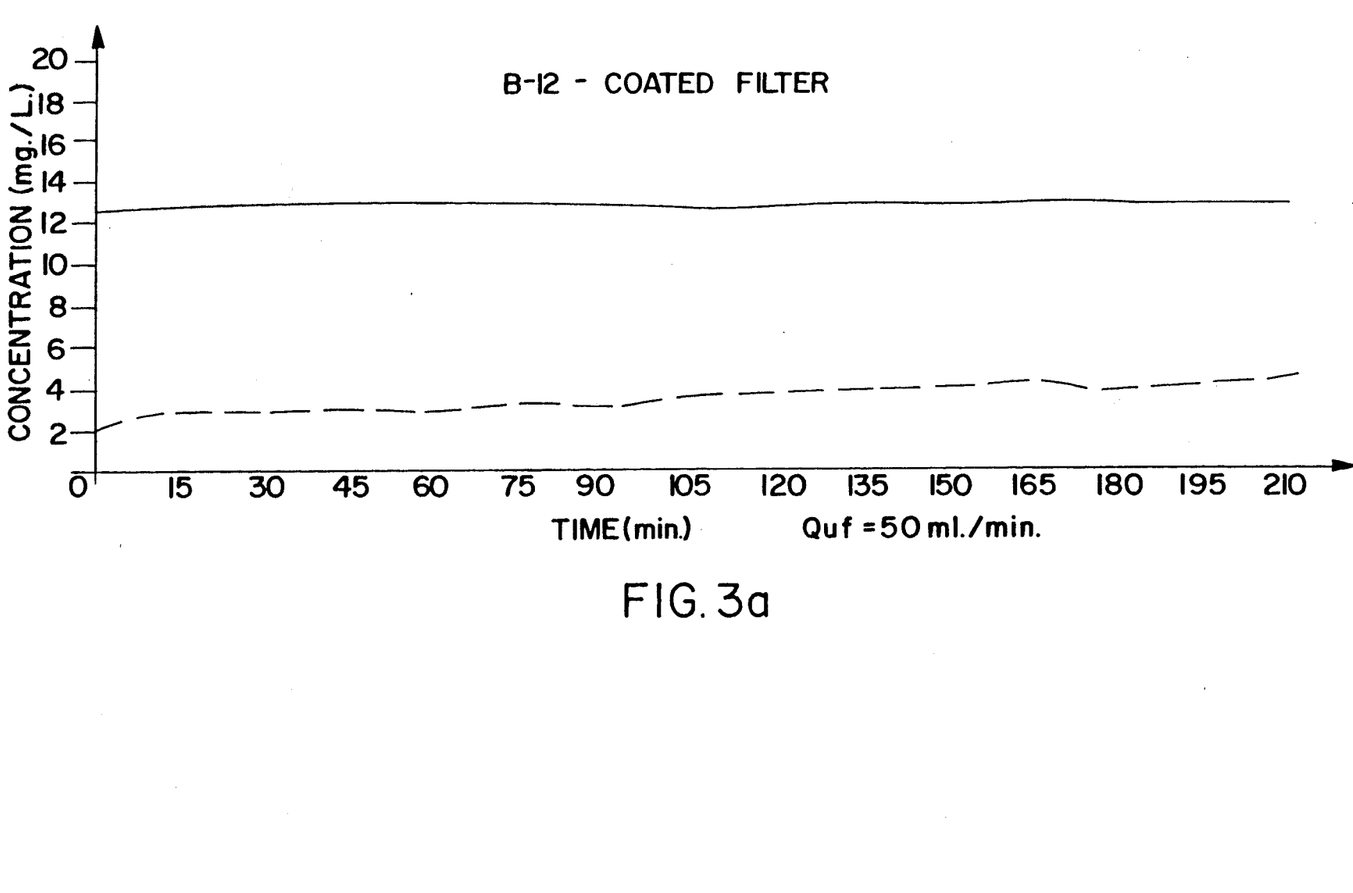
Figure 3B:
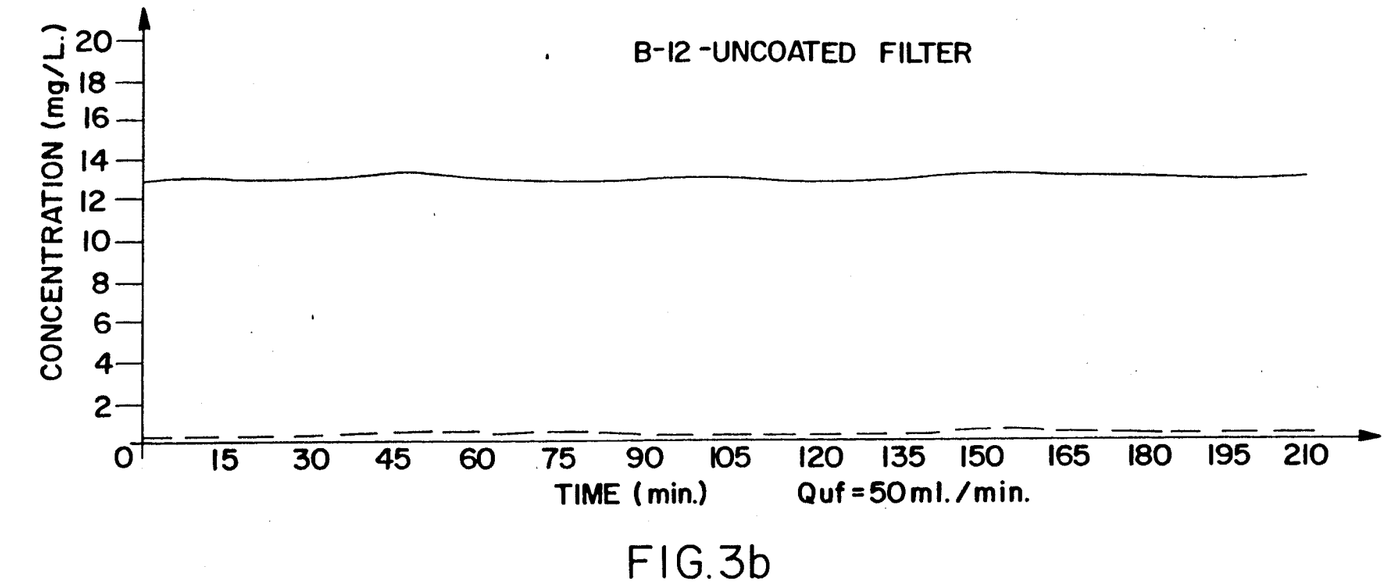

The advantage of the use of this solution is shown specifically by the graphs of FIGS. 2a, 2b and 3a, 3b which show the percentage adsorption of solutes with high molecular weights (typically myoglobin—FIGS. 2a and 2b—and vitamin B12—FIGS. 3a and 3b) as functions of the treatment time t (in minutes). Each graph shows the variation in the concentration of the solute (in mg/l) at the input (continuous line) and at the output (broken lines) of the filter element 11 respectively. The data relate to a constant flow Quf of 50 ml/minute of solution (in vitro). FIGS. 2a and 3a show the data relating to the use of a coated carbon filter (300 g), such as the filters sold under the trade name Emoadsorb by Biotech International of Bologna-Italy. FIGS. 2b and 3b, however, show the results obtained with an uncoated activated carbon filter (Detoxyl 2-85 g). The considerable advantages resulting from the use of uncoated activated carbon can readily be appreciated from the graphs.

Naturally, the principle of the invention remaining the same, the details of construction and forms of embodiment may be varied widely with respect to those described and illustrated, without thereby departing from the scope of the present invention. This is particularly true of the criteria for the construction of the filter 11 which may even be formed according to solutions different from those described, for example, with the use of a filter element other than a carbon filter element, for example, a filter operating by reverse osmosis, etc.

What is claimed is:

1. Equipment for purifying blood by removal of harmful substances contained therein, including a first filter element though which the blood to be purified is passed to effect a purification step by convection with the formation of a quantity of ultrafiltrate which is removed from a blood flow and includes the said harmful substances, a second filter element operatively connected to said first titer element and through which the flow of blood to be purified is passed to effect a purification step by haemodialysis, and compensation means for introducing into the blood flow an infusion solution for compensating, at least partially, for the quantity of ultrafiltrate removed, wherein said compensation means includes a regenerator element which is operatively connected between the first filter element and the compensation means so as to act on the ultrafiltrate to remove said substances therefrom, whereby, after the removal of said substances, at least some of the ultrafiltrate can be used to make up the infusion solution.

2. Equipment according to claim 1, wherein the compensation means is operatively connected between the first filter element and the second filter element.

3. Equipment according to claim 1, wherein the compensation means is downstream of the second filter element.

4. Equipment according to claim 1, wherein the second filter element is downstream of the first filter element.

5. Equipment according to claim 1, wherein discharge means are associated with the first filter element for selectively discharging at least a fraction of the ultrafiltrate from the equipment.

6. Equipment according to claim 1, wherein supply means are associated with the compensation means for supplying a further quantity of infusion solution to be added to the ultrafiltrate output from the regenerator element.

7. Equipment according to claim 1, wherein the regenerator element is a filter.

8. Equipment according to claim 7, wherein the filter works by reverse osmosis.

9. Equipment according to claim 7, wherein the filter works by adsorption.

10. Equipment according to claim 9, wherein the filter is an activated carbon filter.

11. Equipment according to claim 10, wherein the filter is a coated carbon filter.

12. Equipment according to claim 10, wherein the filter is an uncoated carbon filter.

13. Equipment according to claim 7, wherein an auxiliary filter is associated with the filter for retaining any fractions of the material constituting the regenerator element which may be entrained by the ultrafiltrate.

14. Equipment according to claim 1, wherein the regenerator element removes substances with molecular weights of between about 100 and about 20,000 daltons from the ultrafiltrate.

15. Equipment according to claim 1, wherein the regenerator element removes substances with molecular weights of between about 300 and about 1,500 daltons from the ultrafiltrate.

16. A method of producing a quantity of an infusion for compensating, at least partially, for a quantity of ultrafiltrate obtained from a quantity of blood by a haemofiltration purification step, in which the ultrafiltrate transports harmful substances to the removed from the blood, wherein the method includes the step of subjecting the ultrafiltrate to regeneration to remove the substances therefrom so that, after the removal of the substances, at least some of the ultrafiltrate can be used to make up an infusion solution, and a haemodialysis purification step is effected on the blood after compensation by the infusion solution.

17. A method according to claim 16, wherein it includes a haemodialysis purification step effected on the blood before compensation by the infusion solution.

18. A method according to claim 16, wherein it includes the step of selectively discharging at least a fraction of the ultrafiltrate before the regeneration step is carried out.

19. A method according to any one of claim 16, wherein it includes the step of adding a further quantity of infusion solution to the ultrafiltrate after the regeneration step has been carried out.

20. A method according to claim 16, wherein the regeneration step is carried out by filtration.

21. A method according to claim 16, wherein the filtration is carried out by reverse osmosis.

22. A method according to claim 16, wherein the filtration is carried out by adsorption.

23. A method according to claim 16, wherein the filtration takes place through activated carbon.

24. A method according to claim 23, wherein coated carbon is used.

25. A method according to claim 23, wherein uncoated carbon is used.

26. A method according to claim 16, wherein it includes the step of removing primarily substances with molecular weights of between about 100 and about 20,000 daltons from the ultrafiltrate.

27. A method according to claim 16, wherein it includes the step of removing primarily substances with molecular weights of between about 300 and about 1,500 daltons from the ultrafiltrate.

* * * * *

UNITED STATES PATENT AND TRADEMARK OFFICE
CERTIFICATE OF CORRECTION

PATENT NO. : 5,194,157
DATED : March 16, 1993
INVENTOR(S) : Paolo Ghezzi, et. al.

It is certified that error appears in the above-indentified patent and that said Letters Patent is hereby corrected as shown below:

On the Title page, item [75] Inventor's address should be --"Turin" instead of "Turino"
On the Title page, item [73] Assignee's address should be --"Saluggia" instead of "Luggia"

Signed and Sealed this

Fifteenth Day of March, 1994

Attest:

BRUCE LEHMAN

Attesting Officer        Commissioner of Patents and Trademarks